(12) United States Patent
Chen et al.

(10) Patent No.: US 11,660,062 B2
(45) Date of Patent: May 30, 2023

(54) METHOD AND SYSTEM FOR RECOGNIZING CRACKLES

(71) Applicant: BOE TECHNOLOGY GROUP CO., LTD., Beijing (CN)

(72) Inventors: Xue Chen, Beijing (CN); Yong Zhang, Beijing (CN); Shuping Gai, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 830 days.

(21) Appl. No.: 16/081,880

(22) PCT Filed: Dec. 15, 2017

(86) PCT No.: PCT/CN2017/116491
§ 371 (c)(1),
(2) Date: Aug. 31, 2018

(87) PCT Pub. No.: WO2018/176919
PCT Pub. Date: Oct. 4, 2018

(65) Prior Publication Data
US 2021/0007703 A1    Jan. 14, 2021

(30) Foreign Application Priority Data
Mar. 31, 2017 (CN) .......................... 201710210176.3

(51) Int. Cl.
*A61B 7/00* (2006.01)
*G16H 50/20* (2018.01)
*A61B 7/04* (2006.01)
(52) U.S. Cl.
CPC ................ *A61B 7/003* (2013.01); *A61B 7/04* (2013.01); *G16H 50/20* (2018.01)
(58) Field of Classification Search
None
See application file for complete search history.

(56) References Cited

U.S. PATENT DOCUMENTS 6,171,258 B1 * 1/2001 Karakasoglu .......... A61B 5/282
600/529
9,492,096 B2 * 11/2016 Brockway ............... G06F 17/14
(Continued)

FOREIGN PATENT DOCUMENTS

CN    103932733 A  *  7/2014
CN    105662454 A      6/2016
(Continued)

OTHER PUBLICATIONS

Yao, et al., "Research on Recognition Algorithms of Lung Sounds Based on Genetic BP Neural Network", Space Medicine & Medical Engineering, vol. 29, No. 1, Feb. 2016 (Year: 2016).*

(Continued)

*Primary Examiner* — Michael R Bloch
(74) *Attorney, Agent, or Firm* — Arch & Lake LLP

(57) ABSTRACT

The present disclosure provides a method for recognizing crackles, including: processing collected lung sound signal to extract moist rale component for a respiratory cycle; calculating a power spectrum of the moist rale component, and, calculating at least one of a ratio of power of each preset frequency band to total power of all preset frequency bands and the total power of all the preset frequency bands as a frequency domain parameter, and/or calculating at least one of a ratio of the number of occurrence of moist rale and a maximum amplitude of moist rale in the entire inspiratory phase as a time domain parameter; inputting the frequency domain parameter and/or the time domain parameter serving as a parameter feature into a classification model for recognition. The present disclosure further provides a system for recognizing crackles.

14 Claims, 6 Drawing Sheets

(56) References Cited

U.S. PATENT DOCUMENTS

| | | | |
|---|---|---|---|
| 9,687,208 B2 | 6/2017 | Tsai et al. | |
| 2002/0156398 A1* | 10/2002 | Mansy | A61B 7/008 600/586 |
| 2008/0058607 A1* | 3/2008 | Watrous | G16H 70/20 600/300 |
| 2011/0125044 A1* | 5/2011 | Rhee | A61B 5/113 600/534 |
| 2012/0059280 A1* | 3/2012 | Horii | A61B 7/003 600/586 |
| 2013/0060150 A1* | 3/2013 | Song | A61N 1/3627 600/484 |
| 2013/0096464 A1 | 4/2013 | Tanaka et al. | |
| 2013/0178756 A1 | 7/2013 | Suzuki et al. | |
| 2016/0354053 A1* | 12/2016 | Tsai | A61B 5/7275 |
| 2017/0164850 A1* | 6/2017 | Murphy | A61B 5/0245 |

FOREIGN PATENT DOCUMENTS

| | | |
|---|---|---|
| CN | 105913066 A | 8/2016 |
| CN | 103932733 B | 10/2016 |
| CN | 106251880 A | 12/2016 |
| EP | 3 100 675 A1 | 12/2016 |
| WO | WO-2011/155048 A1 | 12/2011 |

OTHER PUBLICATIONS

International Search Report and Written Opinion dated Mar. 16, 2018, from application No. PCT/CN2017/116491.

Chinese Office Action dated Oct. 24, 2019, from application No. 201710210176.3.

Xu, et al., "Detection and Processing of Lung Sound Signal and Its Clinical Application", China Academic Journal Electronic Publishing House, 1992, vol. 15, No. 4, pp. 222-227.

Yao, et al., "Research on Recognition Algorithms of Lung Sounds Based on Genetic BP Neural Network", Space Medicine & Medical Engineering, vol. 29, No. 1, Feb. 2016.

Zheng, et al. "Respiratory phase detection based on one lung sound signal", Tsinghua University, 2008, vol. 48, No. 12, pp. 2136-2140.

* cited by examiner

METHOD AND SYSTEM FOR RECOGNIZING CRACKLES

CROSS REFERENCE

The present application is based upon International Application No. PCT/CN2017/116491, filed on Dec. 15, 2017, which claims the priority of Chinese Patent application No. 201710210176.3, filed on Mar. 31, 2017, and the entire contents thereof are incorporated herein by reference as part of the present application.

TECHNICAL FIELD

The present disclosure relates to a method and a system for recognizing crackles.

BACKGROUND

The lung auscultation sound is closely related to the pathology of the lungs. The cracking sound as a special moist rale is used as the primary clinical clue to prompt interstitial lung disease. Different people have different auditory sensitivities within different frequency bands for their ears, and the moist rale has low intensity, short duration, and wide bandwidth.

At present, digital auscultation is usually used for auxiliary diagnosis, which can make up for the subjectivity and limitations of doctor auscultation.

It should be noted that the information disclosed in the foregoing background section is only for enhancement of understanding of the background of the disclosure and therefore may include information that does not constitute prior art that is already known to those of ordinary skill in the art.

SUMMARY

The present disclosure provides a method for recognizing crackles, which includes the following:
  processing collected lung sound signal to extract moist rale component for a respiratory cycle;
  calculating a power spectrum of the moist rale component and performing at least one of following calculations based on the power spectrum:
  calculating a ratio of power of each preset frequency band in a plurality of preset frequency bands to total power of all preset frequency bands and total power of all preset frequency bands, and selecting at least one of them as a frequency domain parameter; and calculating a ratio of a number of occurrence of moist rale in a late inspiratory phase to a total number of occurrence of moist rale in an entire inspiratory phase and a maximum amplitude of moist rale in the entire inspiratory phase, and selecting at least one of them as a time domain parameter; and
  inputting at least one of an acquired frequency domain parameter and an acquired time domain parameter serving as a parameter feature into a classification model for classification and recognition, so as to recognize crackles.

According to at least one arrangement, the processing collected lung sound signal to extract moist rale component for a respiratory cycle, includes:
  performing wavelet decomposition on the collected lung sound signal to acquire moist rale component and respiratory sound component; and
  determining a respiratory cycle according to the respiratory sound component and extracting the moist rale for the respiratory cycle.

According to at least one arrangement, the wavelet decomposition includes coif2 wavelet decomposition.

According to at least one arrangement, the decomposition level $N \geq 6$.

According to at least one arrangement, the decomposition level N is equal to 9; accumulating components d1-d6 on wavelet to acquire the moist rale component; and accumulating components d7-d9 on wavelet and component a9 on wavelet to acquire the respiratory sound component. 'dn' represents detail component of nth level of the wavelet decomposition, and 'an' represents approximate component of nth level of the wavelet decomposition, where n is an integer and $0<n<10$.

According to at least one arrangement, the determining a respiratory cycle according to the respiratory sound component, includes:
  acquiring an average power graph of the respiratory sound component within a preset frequency range;
  recognizing a peak point and a valley point of the average power graph as an inspiratory phase top point and an expiratory phase switching point respectively, so as to acquire expiratory phase information; and
  determining a stationary expiratory cycle according to the expiratory phase information.

According to at least one arrangement, among the ratios of the power of each preset frequency band to the total power of all preset frequency bands, selecting the ratio corresponding to two frequency bands with largest difference therebetween as the frequency domain parameter.

According to at least one arrangement, the preset frequency bands include 50 Hz-200 Hz and 500 Hz-1000 Hz.

According to at least one arrangement, the late inspiratory phase is ½ of the entire inspiratory phase cycle.

According to at least one arrangement, the processing collected lung sound signal includes filtering the lung sound signal by a band-pass filter.

According to at least one arrangement, the method may include acquiring the lung sound signal by a collector.

The present disclosure provides a system for recognizing crackles, which includes a processor configured to process collected lung sound signal to extract moist rale component for a respiratory cycle, a calculator configured to perform at least one of the following calculations: calculating a ratio of power of each preset frequency band in a plurality of preset frequency bands to total power of all preset frequency bands and total power of all preset frequency bands, and selecting at least one of them as a frequency domain parameter; and calculating a ratio of a number of occurrence of moist rale in a late inspiratory phase to a total number of occurrence of moist rale in an entire inspiratory phase and a maximum amplitude of moist rale in the entire inspiratory phase, and selecting at least one of them as a time domain parameter, and a recognizer configured to input an acquired frequency domain parameter and an acquired time domain parameter serving as a parameter feature into a classification model for classification and recognition, so as to recognize crackles.

According to at least one arrangement, the processor further includes:
a wavelet decomposition circuit configured to perform wavelet decomposition on the collected lung sound signal to acquire moist rale component and respiratory sound component, and an extraction circuit configured to determine a respiratory cycle according to the respiratory sound component, and extract the moist rale for the respiratory cycle.

According to at least one arrangement, the wavelet decomposition includes coif2 wavelet decomposition.

According to at least one arrangement, the extraction circuit is configured to: acquire an average power graph of the respiratory sound component within a preset frequency range; recognize a peak point and a valley point of the average power graph as an inspiratory phase top point and an expiratory phase switching point respectively, so as to acquire expiratory phase information; and determine a stationary expiratory cycle according to the expiratory phase information.

According to at least one arrangement, the calculator is configured to, among the ratios of the power of each preset frequency band to the total power of all preset frequency bands, select the ratio corresponding to two frequency bands with largest difference there-between as the frequency domain parameter.

According to at least one arrangement, the preset frequency bands include 50 Hz-200 Hz and 500 Hz-1000 Hz.

According to at least one arrangement, the late inspiratory phase is ½ of the entire inspiratory phase cycle.

According to at least one arrangement, the processor includes a band-pass filter configured to filter the acquired lung sound signal.

According to at least one arrangement, the processor includes a collector configured to acquire the lung sound signal.

According to at least one arrangement, the collector includes a digital stethoscope.

The present disclosure provides a system for recognizing crackles, which includes:

a memory configured to store a lung sound signal; and a processor configured to:

process the lung sound signal to extract moist rale component for a respiratory cycle; calculate a power spectrum of the moist rale component and perform at least one of following calculations based on the power spectrum: calculating a ratio of power of each preset frequency band in a plurality of preset frequency bands to total power of all preset frequency bands and total power of all preset frequency bands, and selecting at least one of them as a frequency domain parameter; and calculating a ratio of a number of occurrence of moist rale in a late inspiratory phase to a total number of occurrence of moist rale in an entire inspiratory phase and a maximum amplitude of moist rale in the entire inspiratory phase, and selecting at least one of them as a time domain parameter; and input at least one of an acquired frequency domain parameter and an acquired time domain parameter serving as a parameter feature into a classification model for classification and recognition, so as to recognize crackles.

It is to be understood that both the foregoing general description and the following detailed description are exemplary and explanatory only and are not restrictive of the disclosure.

This section provides a general description for various implementations or examples of the technology as described in the present disclosure, which, however, is not a comprehensive disclosure for the entire protection scope or all technical features of the technology of the present disclosure.

BRIEF DESCRIPTION OF THE DRAWINGS

The accompanying drawings, which herein are incorporated in and constitute a part of this specification, illustrate arrangements consistent with the present disclosure, and serve to explain the principles of the disclosure together with the specification. Obviously, the drawings in the following description are merely some of at least one arrangement of the present disclosure. Those skilled in the art can also obtain other drawings based on these drawings without any creative work.

DETAILED DESCRIPTION

In order to enable those skilled in the art to better understand the technical solutions of the present disclosure, the method and system for recognizing crackles provided by the present disclosure will be described in detail below in conjunction with the accompanying drawings.

Figure 1:
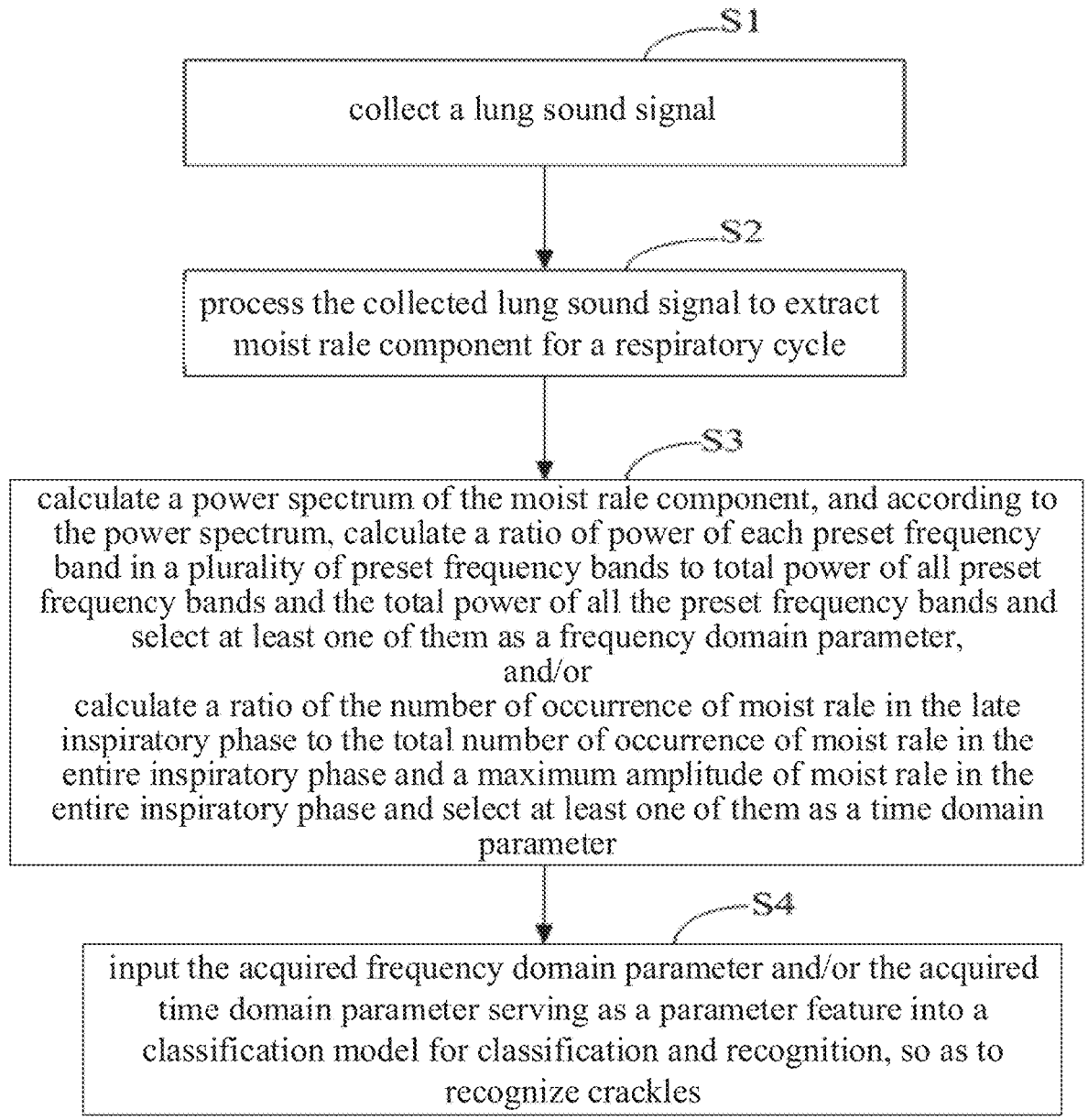
FIG. 1 is a flowchart illustrating a method for recognizing crackles according to at least one arrangement of the present disclosure.

FIG. 1 is a flowchart illustrating a method for recognizing crackles according to at least one arrangement of the present disclosure; referring to FIG. 1, the method for recognizing crackles provided in at least one arrangement includes:

S1: collecting lung sound signals;

S2: processing the collected lung sound signal to extract a moist rale component for a respiratory cycle;

S3: calculating a power spectrum of the moist rale component, and according to the power spectrum, calculating a ratio of power of each preset frequency band in a plurality of preset frequency bands to total power of all preset frequency bands and the total power of all the preset frequency bands and selecting at least one of them as a frequency domain parameter, and/or calculating a ratio of the number of occurrence of moist rale in the late inspiratory phase to the total number of occurrence of moist rale in the entire inspiratory phase and a maximum amplitude of moist rale in the entire inspiratory phase and selecting at least one of them as a time domain parameter.

Specifically, at S3, the present disclosure may use, as a frequency domain parameter, a ratio (Power Ratio, PR) of power of each preset frequency band to total power of all preset frequency bands; or use the total power $PR_{total}$ of all preset frequency bands as a frequency domain parameter; or, use both the ratio (Power Ratio, PR) of the power of each preset frequency band to the total power of all the preset frequency bands and the total power $PR_{total}$ of all the preset frequency bands are as the frequency domain parameters.

The ratio of the number of occurrence of moist rale in the late inspiratory phase for a respiratory cycle to the total number of occurrence of moist rale in the entire inspiratory phase is taken as the time domain parameter; or the maximum amplitude of moist rale in the entire inspiratory phase is taken as the time domain parameter; or both the ratio of the number of occurrence of moist rale in the late inspiratory phase for a respiratory cycle to the total number of occurrence of moist rale in the entire inspiratory phase and the maximum amplitude of moist rale in the entire inspiratory phase are taken as the time domain parameters.

S4: inputting the acquired frequency domain parameter and/or the acquired time domain parameter serving as a parameter feature into a classification model processing inputted parameter feature with the classification model for classification and recognition, and output the recognized crackles.

In this case, the classification model is pre-trained and functions as recognition of crackles according to the frequency domain parameters and/or the time domain parameters. When the classification model is trained by inputting the acquired frequency domain parameter and/or the acquired time domain parameter serving as a parameter feature, the recognition result can be output directly. In this case, the classification model obtained by training may be a support vector machine model (SVM classification model).

It should be noted that in at least one arrangement, S1 may be omitted, that is, the present disclosure is not limited to processing the directly acquired lung sound signal, and the method provided by the present disclosure may process lung sound signals obtained in other way. For example, the present disclosure can also process lung sound signals that are acquired in advance and stored in a computer-readable medium.

In the present disclosure, an inspiratory phase cycle includes an early inspiratory phase and a late inspiratory phase. Correspondingly, the moist rale can be divided into a moist rales in the early inspiratory phase and a moist rale in the late inspiratory phase.

In the present disclosure, according to clinical experience, the tones of crackles are high and strong, the crackles mostly appears in the late inspiratory phase, and the amplitudes and frequencies of the moist rale are related to the pitch and intensity of the tones, thus, in the present disclosure, usage of at least one of the power ratio of the moist rale in different frequency bands and the total power of all preset frequency bands as a frequency domain parameter and/or usage of at least one of the ratios of occurrence of the maximum amplitude of moist rale and the number of occurrence of moist rale in the late inspiratory phase as a time domain parameter can improve the accuracy for recognizing crackles.

According to at least one arrangement, in 2, a band-pass filter is used to filter the acquired lung sound signals, such that the noise such as heart sound signals and power frequency interference can be removed. Furthermore, the band-pass filter may include, but be not limited to, an $8^{th}$-order butterworth band-pass filter whose pass band may be 50 Hz to 2000 Hz.

In addition, in practical applications, when collecting lung sound signals, the most obvious part for the lung sound auscultation can be selected to acquire the digital signal of monopolar lead lung sound. The sampling time can be, but is not limited to, 10 s. The sampling frequency fs can be, but not limited to, 10000 Hz.

Figure 3:
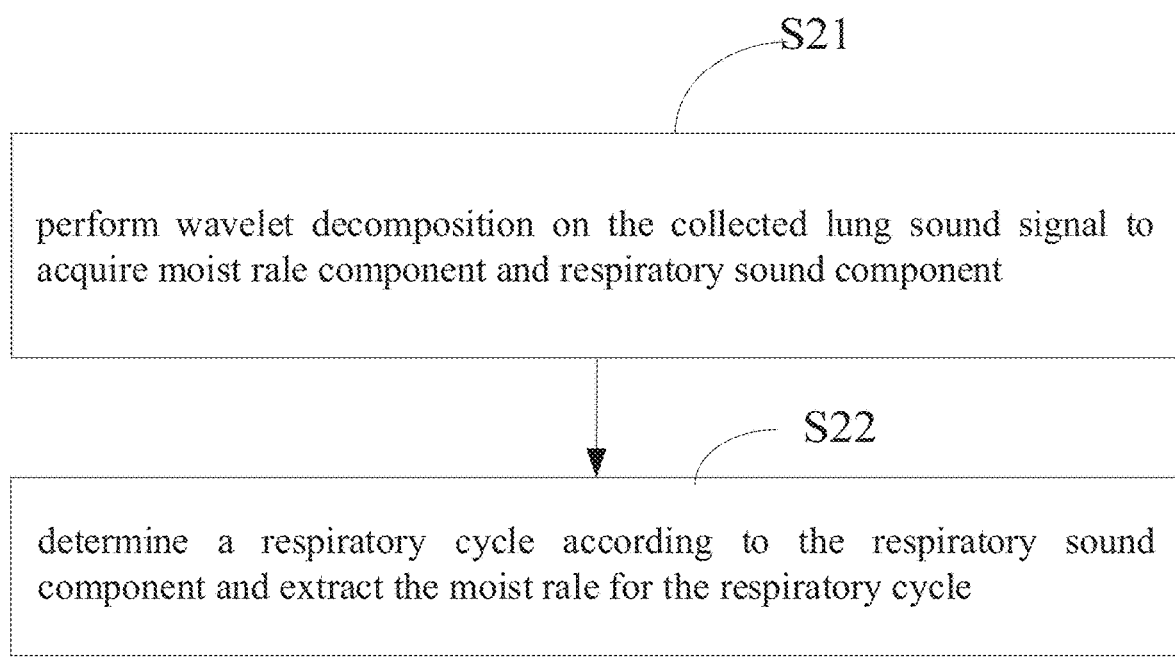
FIG. 3 is a flowchart illustrating S2 in FIG. 1.

According to at least one arrangement, as shown in FIG. 3, in 2, the acquired lung sound signal is processed to extract a moist rale component for a respiratory cycle and this can be realized by the following S21 and S22.

In S21, wavelet decomposition is performed on the collected lung sound signal to acquire a moist rale component and respiratory sound component.

In S22, a respiratory cycle is determined according to the respiratory sound component and the moist rale for the respiratory cycle is extracted.

In the present disclosure, the wavelet decomposition method is used to process the collected lung sound signals, such that the procedure is simpler, and thus the efficiency for recognizing cracking sound can be improved.

According to at least one arrangement, the wavelet decomposition may be coiflet wavelet (short for coif N) decomposition. The reason why the coif2 wavelet decomposition is adopted in the present disclosure is that the coif2 wavelet possesses a better symmetry, which may avoid the waveform distortion of moist rale component and respiratory sound component. Thus, the accuracy for recognizing crackles can be further improved. In wavelet decomposition process, the original signal S is divided into two components, where one with high frequency is called the detail component d1 and the other one with low frequency is called the approximate component a1; followed by secondary division of the component with low frequency into two components, where one with high frequency is called the detail component d2 and the other one with low frequency is called the approximate component a2; and so on, until the predetermined decomposition level N is realized.

Alternatively, the waveform distortion of moist rale component may be avoided preferably when the decomposition level N of coif2 wavelet decomposition is greater than 6.

According to at least one arrangement, the decomposition level N is equal to 9, components d1-d6 on wavelet is accumulated to acquire the moist rale component and components d7-d9 on wavelet and component a9 on wavelet is accumulated to acquire the respiratory sound component. In this case, 'dn' represents detail component of nth level of the wavelet decomposition, and 'an' represents approximate component of nth level of the wavelet decomposition, where n is an integer and 0<n<10. According to correspondence of coif2 wavelet decomposition, the high frequency band of nth-level component corresponds to the range of $fs/2^{n+1}$~$fs/2^n$, where $1 \leq n \leq N$. Although the frequency band of the crackles is mainly within 200 Hz-1000 Hz, the tone of crackles is higher than other moist rales and the frequency band of the moist rale is generally within 50 Hz-2500 Hz, and thus, selection of components d1-d6 on wavelet to be accumulated for acquisition of the moist rale component and components d7-d9 on wavelet and component a9 on wavelet to be accumulated for acquisition of the respiratory sound component is good for avoidance from the waveform distortion of the moist rale component and the respiratory sound component.

Figure 2:
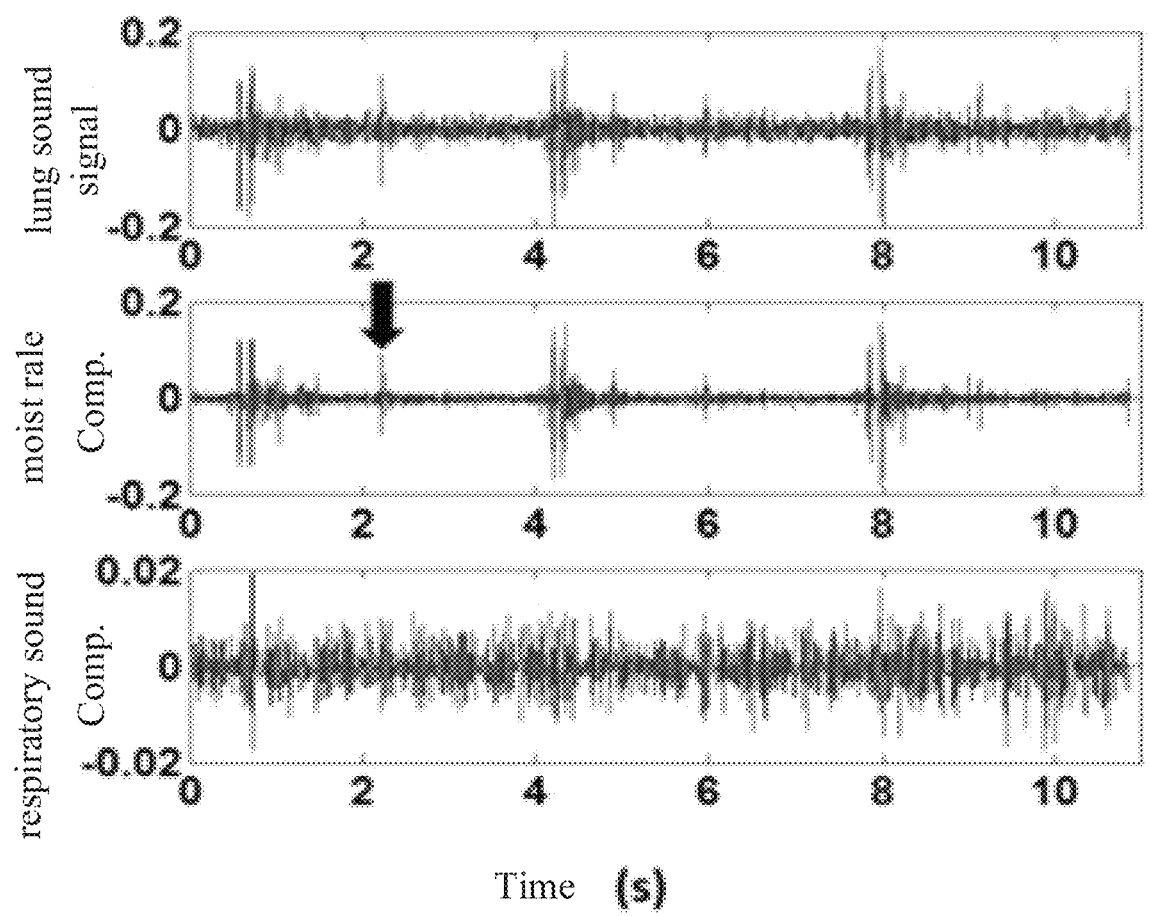
FIG. 2 is a schematic diagram illustrating the relationship between a lung sound signal, a moist rale component, and a respiratory sound component in the present disclosure.

Specifically, referring to FIG. 2, FIG. 2 is a schematic diagram illustrating the relationship between a lung sound signal, a moist rale component, and a respiratory sound component in the present disclosure. As can be seen from FIG. 2 that a moist rale component is included in a lung sound signal and can be seen clearly. As shown by the black arrows, waveform distortions of the moist rale component and the respiratory sound component can be well avoided.

What is explained here is that in practical applications, wavelet decomposition can also use other decomposition methods.

Figure 4:
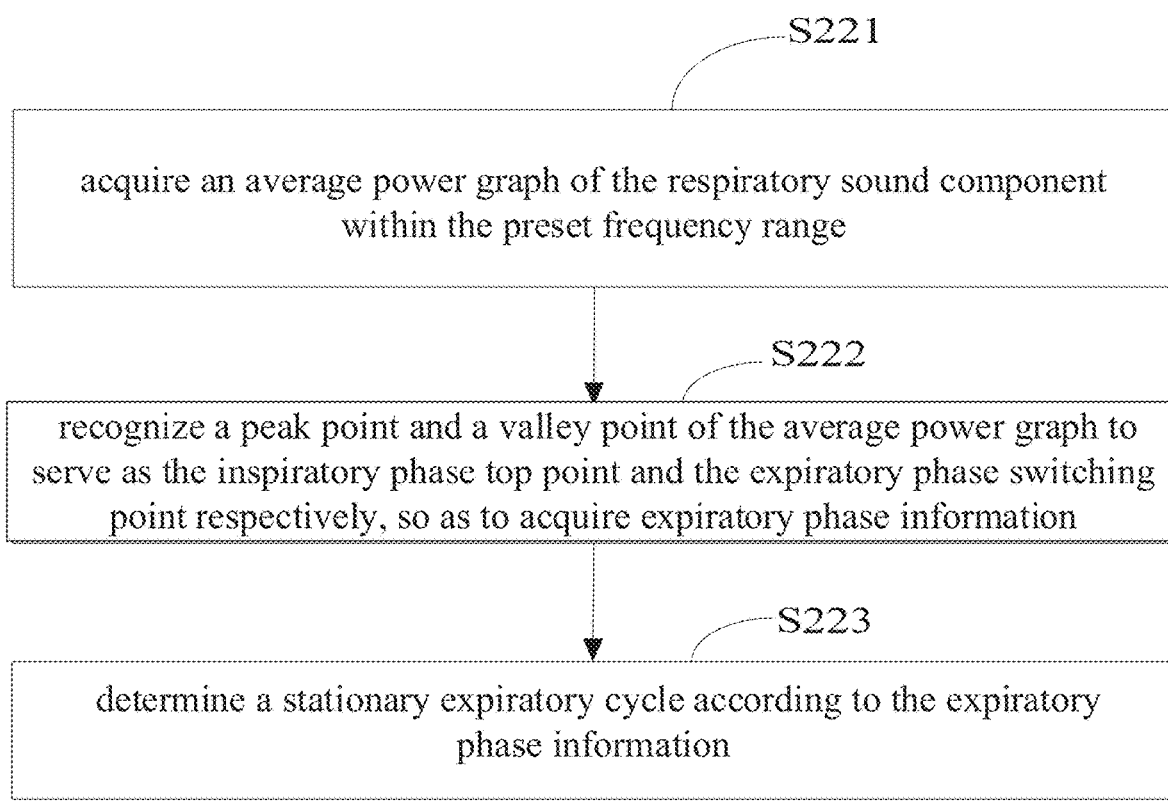
FIG. 4 is a flowchart illustrating S22 in FIG. 3.

According to at least one arrangement, as shown in FIG. 4, the S22 of determination of a respiratory cycle according to the respiratory sound component can be realized by the following S221 and S223.

In S221, an average power graph of the respiratory sound component within the preset frequency range is acquired.

In this case, the preset frequency range may be, but be not limited to, 150-450 Hz. The reason why the frequency band range of 150 Hz-450 Hz is selected is that the energy difference of the expiratory phase in this range is the most significant.

Specifically, in order to obtain the average power graph of the respiratory sound component within the preset frequency range, the respiratory sound component may be first divided into a plurality of windows with 100 ms duration and the window-move is 75 ms. The Fourier transform of the respiratory sound signal in each window is calculated by the following formula (1) and the square of its modulus is taken as the short-term power spectrum of the respiratory sound signal:

$$p(t_n, f_k) = \left| \sum_{m=t_nD-(T/2)}^{t_nD+(T/2)-1} w(t_nD - m)x(m)e^{-j2\pi f_k m/T} \right|^2 \quad (1)$$

Where, x(m) is the m-th window of the respiratory sound component, $t_n$ and $f_k$ are time and frequency respectively, is a moving window function with duration T and window-move D. In this case, the present disclosure uses a Hanning widow and other window functions are also possible.

Figure 5:
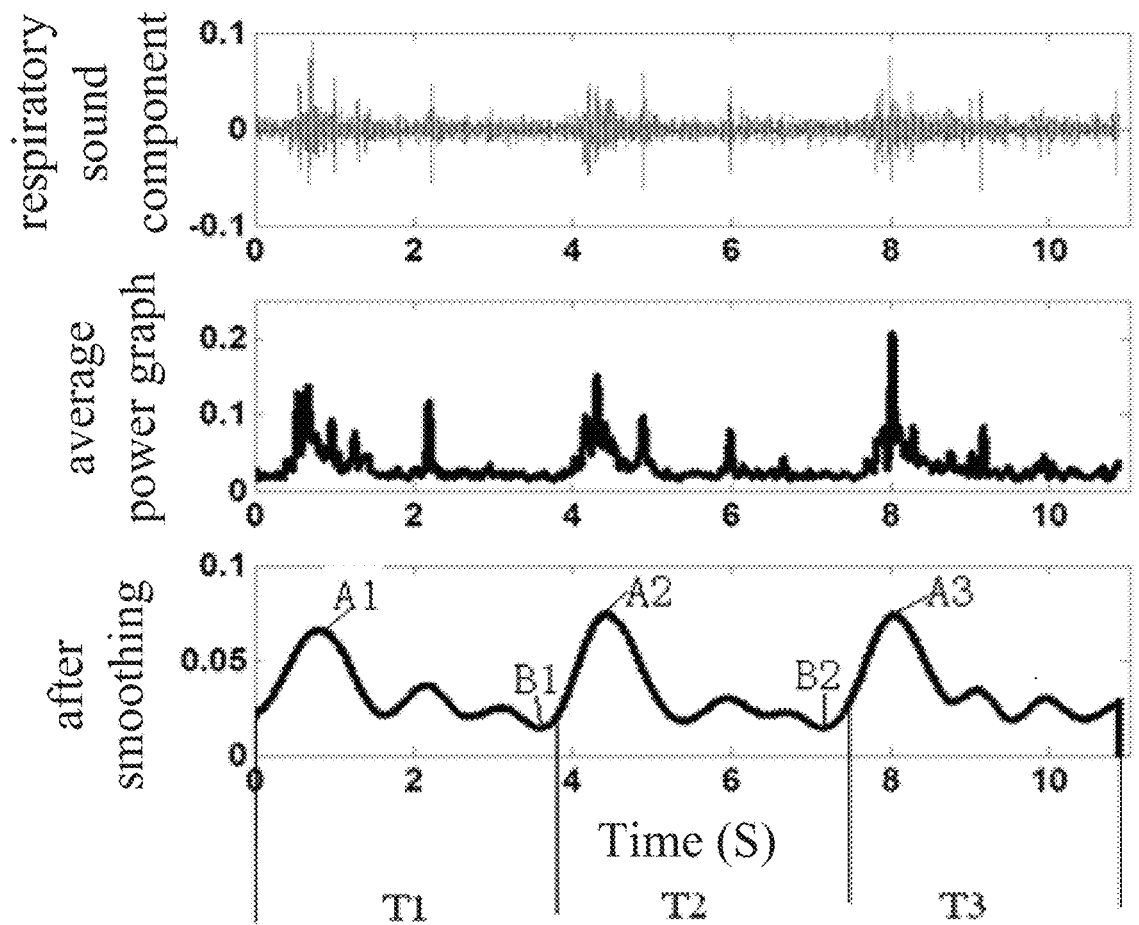
FIG. 5 is a graph illustrating an average power of a respiratory sound component.

Next, the average power graph of the respiratory sound component within the frequency band of 150 Hz to 450 Hz is calculated according to the following formula (2), as shown in FIG. 5.

$$\overline{p(t_n)} = \frac{\sum_{f_k=f_{low}}^{f_{high}} p(t_n, f_k)}{f_{high} - f_{low}} \quad (2)$$

Where, $f_{high}$ is 450 Hz, and $f_{low}$ is 150 Hz.

In S222, a peak point and a valley point of the average power graph are recognized as the inspiratory phase top point (A1, A2 and A3 as in FIG. 6) and the expiratory phase switching point (B1 and B2 as in FIG. 6) respectively, so as to acquire expiratory phase information.

In S223, a stationary expiratory cycle is determined according to the expiratory phase information.

In this case, a respiratory cycle is the duration from the starting time of the waveform when the inspiratory top point occurs to the ending time of the waveform when the expiratory phase switching point occurs, as shown by T1-T3 in FIG. 5; the so-called stationary respiratory cycle refers to the relatively stationary respiratory cycle of the power graph, T2 is more smooth than T1, and thus, T2 is selected as a stationary respiratory cycle.

In the present disclosure, a stationary respiratory cycle is necessary because a smooth respiratory cycle can better reflect the condition of the patient's lungs, thus contributing to the improvement of the accuracy for recognizing the cracking sound.

According to at least one arrangement, among the ratios of the power of each preset frequency band to the total power of all preset frequency bands, the present disclosure may select the ratio corresponding to the two frequency bands with the largest difference there-between as the frequency domain parameter, which is equivalent to removing some interference factor caused by similar frequency band, and thus, the accuracy for recognizing the cracking sound can be improved.

Further alternatively, the preset frequency band includes 50 Hz to 200 Hz and 500 Hz to 1000 Hz, since the ratios of the power to the total power of all the preset frequency bands corresponding to the two frequency bands has the largest difference. In this case, specifically, the preset frequency band may include, but is not limited to, four preset frequency bands of 50 Hz to 200 Hz, 200 Hz to 500 Hz, 500 Hz to 1000 Hz, and 1000 Hz to 1500 Hz.

According to at least one arrangement, the late inspiratory phase described herein is ½ of the entire inspiratory phase cycle, i.e., the inspiratory phase is evenly divided into the early inspiratory phase and the late inspiratory phase, so that it can be ensured as much as possible that crackling sounds are located within the late inspiratory phase, thus improving the accuracy for recognizing cracking sounds.

Specifically, in S3, a power spectrum of moist rale component for a respiratory cycle can be calculated by using, but not limited to, a multi-order autoregressive model. For example, in at least one arrangement, a 14-order autoregressive model can be used to calculate the power spectrum of the moist rale component for the respiratory cycle.

Figure 6:
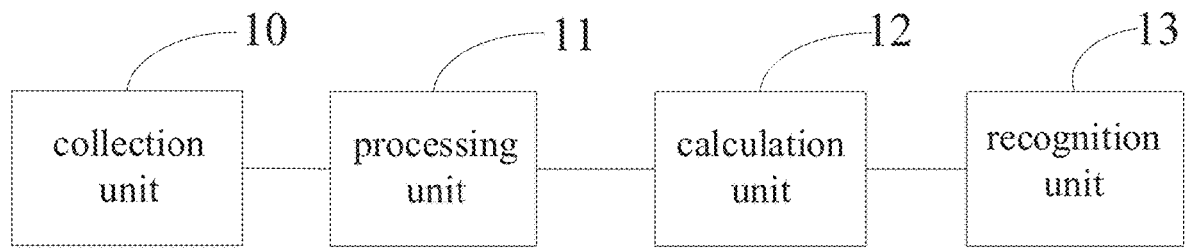
FIG. 6 is a block diagram illustrating a system for recognizing crackles according to at least one arrangement of the present disclosure.

FIG. 6 is a block diagram illustrating a system for recognizing crackles according to at least one arrangement of the present disclosure. Referring to FIG. 6, the system includes a collection unit 10, a processing unit 11, a calculation unit 12 and a recognition unit 13.

The collection unit 10 is configured to acquire a lung sound signal.

The processing unit 11 is configured to process the collected lung sound signal to extract moist rale component for a respiratory cycle.

The calculation unit 12 is configured to calculate a power spectrum of the moist rale component; calculate, according to the power spectrum, a ratio of power of each preset frequency band in a plurality of preset frequency bands to total power of all preset frequency bands and the total power of all the preset frequency bands and select at least one of them as a frequency domain parameter; or/and calculate a ratio of the number of occurrence of moist rale in the late inspiratory phase for respiratory cycle to the total number of occurrence of moist rale in the entire inspiratory phase and a maximum amplitude of moist rale in the entire inspiratory phase and select at least one of them as a time domain parameter.

The recognition unit 13 is configured to input the acquired frequency domain parameter and the acquired time domain parameter serving as a parameter feature into a classification model for classification and recognition, so as to recognize crackles.

It should be noted that in at least one arrangement, the collection unit 10 may be omitted, that is, the present disclosure is not limited to processing directly acquired lung sound signals, and the system for recognizing crackles provided by the present disclosure may process lung sound signals acquired in other way. For example, the present disclosure can also process lung sound signals that are acquired in advance and stored in a computer-readable medium.

The above units of the present disclosure may be implemented by corresponding hardware. For example, the collection unit 10 may include a collector (e.g., an audio collector) for collecting lung sound signals. More specifically, the collector may include a digital stethoscope, however, the present disclosure is not limited thereto. In addition, the processing unit may include a processor configured to process a lung sound signal. In addition, the calculation unit 12 may include a calculator configured to perform further calculations on moist rale components. The processor and the calculator may be specifically configured by a logic circuit, an integrated circuit, a dedicated processor, a general-purpose processor, or the like, but the present disclosure is not limited thereto.

In the present disclosure, according to clinical experience, the tones of crackles are high and strong, the crackles mostly appears in the late inspiratory phase, and the amplitudes and frequencies of the moist rale are related to the pitch and intensity of the tones, thus, in the present disclosure, usage of at least one of the power ratio the moist rale in different frequency bands and the total power of all preset frequency bands as a frequency domain parameter and/or usage of at least one of the ratios of occurrence of the maximum amplitude of moist rale and the number of occurrence of moist rale in the late inspiratory phase as a time domain parameter can improve the accuracy for recognizing crackles.

Figure 7:
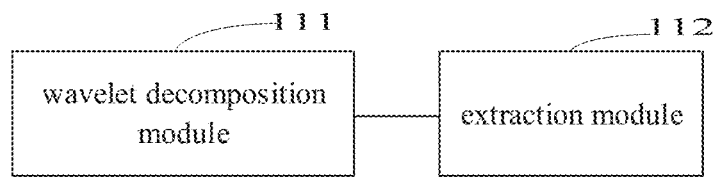
FIG. 7 is a block diagram illustrating the processing unit in FIG. 6.

According to at least one arrangement, as shown in FIG. 7, the processing unit 11 includes a wavelet decomposition module 111 and an extraction module 112.

The wavelet decomposition module 111 is configured to perform wavelet decomposition on the collected lung sound signal to acquire moist rale component and respiratory sound component.

The extraction module 112 is configured to determine a respiratory cycle according to the respiratory sound component, and extract the moist rale for the respiratory cycle.

In the present disclosure, the above-mentioned module may be constituted by a circuit that performs a corresponding function. For example, the wavelet decomposition module 111 may be composed of a wavelet decomposition circuit configured to perform wavelet decomposition on signals. In addition, the extraction module 112 may consist of an extraction circuit configured to extract moist rale. More specifically, the wavelet decomposition circuit and the extraction circuit may be specifically configured by a logic circuit, an integrated circuit, a dedicated processor, a general-purpose processor, or the like, but the present disclosure is not limited thereto.

In the present disclosure, the wavelet decomposition method is used to process the collected lung sound signals, such that the procedure is simpler, and thus the efficiency for recognizing crackles can be improved.

According to at least one arrangement, the wavelet decomposition includes coif2 wavelet decomposition. The reason why the coif2 wavelet decomposition is adopted in the present disclosure is that the coif2 wavelet possesses a better symmetry, which may avoid the waveform distortion of the refactor moist rale component and the refactor respiratory sound component, thus, the accuracy for recognizing crackles can be further improved.

According to at least one arrangement, the decomposition level N is greater than 6.

Furthermore, the decomposition level N is equal to 9, components d1-d6 on wavelet is accumulated to acquire the moist rale component and components d7-d9 on wavelet and component a9 on wavelet is accumulated to acquire the respiratory sound component. In this case, 'dn' represents detail component of nth level of the wavelet decomposition, and 'an' represents approximate component of nth level of the wavelet decomposition, where n is an integer and 0<n<10.

According to at least one arrangement, the extraction module 112 is configured to acquire an average power graph of the respiratory sound component within the preset frequency range; recognize a peak point and a valley point of the average power graph to serve as the inspiratory phase top point and the expiratory phase switching point respectively, so as to acquire expiratory phase information; and determine a stationary expiratory cycle according to the expiratory phase information. In the present disclosure, a stationary respiratory cycle is necessary because a smooth respiratory cycle can better reflect the condition of the patient's lungs, thus contributing to the improvement of the accuracy for recognizing the cracking sound.

According to at least one arrangement, the calculation unit 12 is configured to, among the ratios of the power of each preset frequency band to the total power of all preset frequency bands, select the ratio corresponding to the two frequency bands with the largest difference there-between as the frequency domain parameter. In the present disclosure, selection of the ratio corresponding to the two frequency bands with the largest difference there-between as the frequency domain parameter may result in removal of some interference factor caused by similar frequency band, and thus, the accuracy for recognizing the cracking sound can be improved.

In this case, the preset frequency bands include 50 Hz-200 Hz and 500 Hz-1000 Hz, since the ratios of the power to the total power of all the preset frequency bands corresponding to the two frequency bands has the largest difference.

According to at least one arrangement, the late inspiratory phase described herein is ½ of the entire inspiratory phase cycle, such that it can be ensured as much as possible that crackling sounds are located within the late inspiratory phase, thus improving the accuracy for recognizing cracking sounds.

According to at least one arrangement, the system for recognizing crackles according to at least one arrangement may further include a band-pass filter configured to filter the lung sound signal.

It should be noted that the system for recognizing crackles provided by at least one arrangement is a product arrangement corresponding to the method for recognizing crackles provided in the previous arrangement. In the foregoing arrangement, the detailed description has been made on the method for recognizing crackles. For related features of the system and the method for recognizing crackles, please refer to the above arrangements, and these will not be described herein.

In addition, another aspect of the present disclosure provides a system for recognizing crackles, which includes:

a memory configured to store a lung sound signal; and a processor configured to perform the method for recognizing crackles according to any one of the above arrangements.

The present disclosure have the following advantageous effects.

According to clinical experience, the tones of crackles are high and strong, the crackles mostly appears in the late inspiratory phase, and the amplitudes and frequencies of the moist rale are related to the pitch and intensity of the tones, thus, in the present disclosure, usage of at least one of the power ratio of the moist rale in different frequency bands and the total power of all preset frequency bands as a frequency domain parameter and/or usage of at least one of the ratios of occurrence of the maximum amplitude of moist rale and the number of occurrence of moist rale in the late inspiratory phase as a time domain parameter can improve the accuracy for recognizing crackles.

It can be understood that the above arrangements are merely exemplary arrangements employed for illustrating the principle of the present disclosure, but the present disclosure is not limited thereto. For a person of ordinary skill in the art, various variations and improvements may be made without departing from the spirit and essence of the present disclosure, and these variations and improvements are also considered to be within the protection scope of the present disclosure.

What is claimed is:

1. A method for treating pathology of lungs by recognizing crackles, comprising:
processing collected lung sound signal to extract a moist rale component for a respiratory cycle;
calculating a power spectrum of the moist rale component and performing at least one of following calculations based on the power spectrum:
calculating a plurality of ratios and a total power of a plurality of preset frequency bands, each ratio of the plurality of ratios being defined as a power of one of the plurality of preset frequency bands to the total power of the plurality of preset frequency bands, and selecting at least one of the plurality of ratios or the total power as a frequency domain parameter; and
calculating an additional ratio of a number of occurrence of a first plurality of moist rales in a late inspiratory phase to a total number of occurrence of a second plurality of moist rales in an entire inspiratory phase, and calculating a maximum amplitude of one of the second plurality of moist rales in the entire inspiratory phase, and selecting at least one of the additional ratio or the maximum amplitude as a time domain parameter; and
inputting at least one of the selected frequency domain parameter and the selected time domain parameter serving as a parameter feature into a support vector machine model (SVM) classification model; processing inputted parameter feature with the SVM classification model for classification; and recognition and outputting recognized crackles by the SVM classification model,
wherein the processing collected lung sound signal to extract the moist rale component for the respiratory cycle, comprises:
performing wavelet decomposition on the collected lung sound signal to acquire the moist rale component and a respiratory sound component; and
determining the respiratory cycle according to the respiratory sound component and extracting the moist rale component for the respiratory cycle,
wherein the wavelet decomposition comprises coif2 wavelet decomposition and a decomposition level N of the wavelet decomposition is equal to 9, and
wherein the method further comprises: accumulating components d1-d6 on wavelet to acquire the moist rale component; and accumulating components d7-d9 on wavelet and component a9 on wavelet to acquire the respiratory sound component, wherein 'dn' represents detail component of nth level of the wavelet decomposition, and 'an' represents approximate component of nth level of the wavelet decomposition, where n is an integer and 0<n<10.

2. The method according to claim 1, wherein the determining the respiratory cycle according to the respiratory sound component, comprises:
acquiring an average power graph of the respiratory sound component within a preset frequency range;
recognizing a peak point and a valley point of the average power graph as an inspiratory phase top point and an expiratory phase switching point respectively, so as to acquire expiratory phase information; and
determining a stationary expiratory cycle according to the expiratory phase information.

3. The method according to claim 1, wherein, among the plurality of ratios, selecting the ratios corresponding to two frequency bands having largest difference there-between as the frequency domain parameter.

4. The method according to claim 1, wherein the late inspiratory phase is ½ of the entire inspiratory phase.

5. The method according to of claim 1, wherein the processing collected lung sound signal comprises:
filtering the lung sound signal by a band-pass filter.

6. The method according to claim 1, wherein the SVM classification model is acquired by pre-training and the SVM classification model is configured to recognize crackles according to at least one of the frequency domain parameter and the time domain parameter.

7. The method according to claim 1, further comprising:
acquiring the lung sound signal by a collector.

8. A system for treating pathology of lungs by recognizing crackles, comprising:
a processor configured to process collected lung sound signal to extract moist rale component for a respiratory cycle;
a calculator configured to perform at least one of the following calculations:
calculating a ratio of power of each preset frequency band in a plurality of preset frequency bands to total power of all preset frequency bands and total power of all preset frequency bands, and selecting at least one of the ratio or the total power as a frequency domain parameter; and
calculating an additional ratio of a number of occurrence of moist rale in a late inspiratory phase to a total number of occurrence of moist rale in an entire inspiratory phase, and calculating a maximum amplitude of moist rale in the entire inspiratory phase, and selecting at least one of the additional ratio or the maximum amplitude as a time domain parameter; and
a recognizer configured to input the selected frequency domain parameter and/or the selected time domain parameter serving as a parameter feature into a support vector machine model (SVM) classification model; process inputted parameter feature with the SVM classification model for classification and recognition; and output recognized crackles by the SVM classification model,
wherein the processor comprises:
a wavelet decomposition circuit configured to perform wavelet decomposition on the collected lung sound signal to acquire moist rale component and respiratory sound component; and
an extraction circuit configured to determine the respiratory cycle according to the respiratory sound component, and extract the moist rale for the respiratory cycle,
wherein the wavelet decomposition comprises coif2 wavelet decomposition, and a decomposition level N of the wavelet decomposition is equal to 9,
wherein the processor is further configured to: accumulate components d1-d6 on wavelet to acquire the moist rale component; and accumulate components d7-d9 on wavelet and component a9 on wavelet to acquire the respiratory sound component, wherein 'dn' represents detail component of nth level of the wavelet decomposition, and 'an' represents approximate component of nth level of the wavelet decomposition, where n is an integer and 0<n<10.

9. The system according to claim 8, wherein the extraction circuit is configured to:
acquire an average power graph of the respiratory sound component within a preset frequency range;
recognize a peak point and a valley point of the average power graph as an inspiratory phase top point and an expiratory phase switching point respectively, so as to acquire expiratory phase information; and
determine a stationary expiratory cycle according to the expiratory phase information.

10. The system according to claim 8, wherein the calculator is configured to, among the ratios of the power of each preset frequency band to the total power of all preset frequency bands, select the ratios corresponding to two frequency bands having largest difference there-between as the frequency domain parameter.

11. The system according to claim 8, wherein the late inspiratory phase is ½ of the entire inspiratory phase.

12. The system according to claim 8, further comprising a band-pass filter configured to filter the collected lung sound signal.

13. The system according to claim 8, further comprising a collector configured to acquire the lung sound signal.

14. A system for treating pathology of lungs by recognizing crackles, comprising:
a memory configured to store a lung sound signal;
a processor configured to:
process the lung sound signal to extract moist rale component for a respiratory cycle;
calculate a power spectrum of the moist rale component and perform at least one of following calculations based on the power spectrum:
calculating a ratio of power of each preset frequency band in a plurality of preset frequency bands to total power of all preset frequency bands and total power of all preset frequency bands, and selecting at least one of the ratio or the total power as a frequency domain parameter; and
calculating an additional ratio of a number of occurrence of moist rale in a late inspiratory phase to a total number of occurrence of moist rale in an entire inspiratory phase, and calculating a maximum amplitude of moist rale in the entire inspiratory phase, and selecting at least one of the additional ratio or the maximum amplitude as a time domain parameter; and
input at least one of the selected frequency domain parameter and the selected time domain parameter serving as a parameter feature into a support vector machine model (SVM) classification model; process inputted parameter feature with the SVM classification model for classification and recognition; and output recognized crackles by the SVM classification model,
wherein the processing the lung sound signal to extract moist rale component for the respiratory cycle, comprises:
performing wavelet decomposition on the collected lung sound signal to acquire the moist rale component and a respiratory sound component; and
determining the respiratory cycle according to the respiratory sound component and extracting the moist rale component for the respiratory cycle,
wherein the wavelet decomposition comprises coif2 wavelet decomposition, and a decomposition level N of the wavelet decomposition is equal to 9,
wherein the processor is further configured to: accumulate components d1-d6 on wavelet to acquire the moist rale component; and accumulate components d7-d9 on wavelet and component a9 on wavelet to acquire the respiratory sound component, wherein 'dn' represents detail component of nth level of the wavelet decomposition, and 'an' represents approximate component of nth level of the wavelet decomposition, where n is an integer and 0<n<10.

* * * * *